United States Patent
Alfano et al.

(10) Patent No.: US 7,986,989 B2
(45) Date of Patent: Jul. 26, 2011

(54) PHOSPHORESCENCE AND FLUORESCENCE SPECTROSCOPY FOR DETECTION OF CANCER AND PRE-CANCER FROM NORMAL/BENIGN REGIONS

(75) Inventors: Robert R. Alfano, Bronx, NY (US); Aleksandra Alimova, Bronx, NY (US); Alvin Katz, Bronx, NY (US)

(73) Assignee: The Research Foundation of the City University of New York, New York, NY (US)

( * ) Notice: Subject to any disclaimer, the term of this patent is extended or adjusted under 35 U.S.C. 154(b) by 672 days.

(21) Appl. No.: 11/521,170

(22) Filed: Sep. 14, 2006

(65) Prior Publication Data
US 2007/0083122 A1  Apr. 12, 2007

Related U.S. Application Data

(60) Provisional application No. 60/725,670, filed on Sep. 29, 2005.

(51) Int. Cl.
*A61B 6/00* (2006.01)
*G01N 21/64* (2006.01)
*G01N 21/76* (2006.01)

(52) U.S. Cl. .............. 600/476; 600/477; 422/82.08; 436/172

(58) Field of Classification Search .............. 422/82.08; 436/172
See application file for complete search history.

(56) References Cited

U.S. PATENT DOCUMENTS

| | | | | |
|---|---|---|---|---|
| 5,413,108 A * | 5/1995 | Alfano | | 600/478 |
| 6,091,985 A * | 7/2000 | Alfano et al. | | 600/476 |
| 7,103,402 B2 * | 9/2006 | Vo-Dinh | | 600/476 |
| 7,519,411 B2 * | 4/2009 | Long | | 600/407 |
| 2003/0236458 A1 * | 12/2003 | Hochman | | 600/431 |
| 2004/0082863 A1 * | 4/2004 | McGreevy et al. | | 600/476 |
| 2004/0092824 A1 * | 5/2004 | Stamnes et al. | | 600/473 |
| 2008/0230715 A1 * | 9/2008 | Nielsen et al. | | 250/458.1 |

\* cited by examiner

*Primary Examiner* — Long V Le
*Assistant Examiner* — Angela M Hoffa
(74) *Attorney, Agent, or Firm* — The Farrell Law Firm, P.C.

(57) ABSTRACT

The present application is directed to methods for detecting cancerous, pre-cancerous and benign/normal tissue using phosphorescence or the combination of fluorescence and phosphorescence emission from the tissue excited in 280 to 340 nm range. In particular, the application describes methods using a ratio of intensity of fluorescence emission to intensity of phosphorescence emission to provide a rapid cancer, pre-cancer and benign detection method. Normal human breast and prostate tissue, excited in 270 to 300 nm range, express the emission signatures at 340 nm, 440 nm and 500 nm. Cancerous tissue shows only minor emissions at 500 nm, thus the ratio of 340 nm peak to 500 nm peak emission intensities provides information about malignancy of a tissue. Fiber optic based instrumentation can be used to collect the luminescence signal from an area of a tissue less than 1 mm in diameter and using the described method can be screened to determine the state of the tissue sample taken. The combination of fiber optics and 2D translation stage provides 2D maps of intensity's ratio of the tissue surface and aids in localizing the malignancy region of the tissue.

15 Claims, 11 Drawing Sheets

PHOSPHORESCENCE AND FLUORESCENCE SPECTROSCOPY FOR DETECTION OF CANCER AND PRE-CANCER FROM NORMAL/BENIGN REGIONS

CROSS-REFERENCE TO RELATED APPLICATIONS

The present invention claims priority from U.S. Provisional Patent Application Ser. No. 60/725,670, filed Sep. 29, 2005, the contents of which are hereby incorporated by reference.

FIELD OF THE INVENTION

The present invention is directed to methods for distinguishing cancerous and pre-cancerous tissues from benign/normal tissues in vivo or ex vivo using phosphorescence or combination of phosphorescence and fluorescence spectroscopy.

BACKGROUND OF INVENTION

Using fluorescence to detect cancerous tissue is not new. R. Alfano et.al.[1,2] first demonstrated that fluorescence can be used to detect cancer in tissue. Ultraviolet (UV) and visible light can be used to excite fluorescence of key molecules to detect cancerous and pre-cancerous tissue from normal tissue or benign tissue. UV luminescence spectroscopy of biomolecules is a powerful tool to study biological specimens, such as bacteria, viruses and biological tissues[3-7]. UV light in the 250 nm to 400 nm range allows exciting the natural fluorophore in a biological specimen, such as amino acids in proteins and/or NADH. The present invention provides novel methods using phosphorescence data of excited tissue to rapidly detect cancer.

UV illumination in an absorption bands excites molecules of a specimen and radiative relaxation results in light emission, red shifted relative to the absorption wavelength. Emission of light occurs as fluorescence between singlet states and phosphorescence from the triplet to the singlet state. Fast relaxation ($\sim 10^{-9}$-$10^{-6}$ sec) of light emission is associated with fluorescence and longer life-time ($\sim 1$ to $10^{-6}$ sec) relaxation is associated with phosphorescence.

Figure 1:
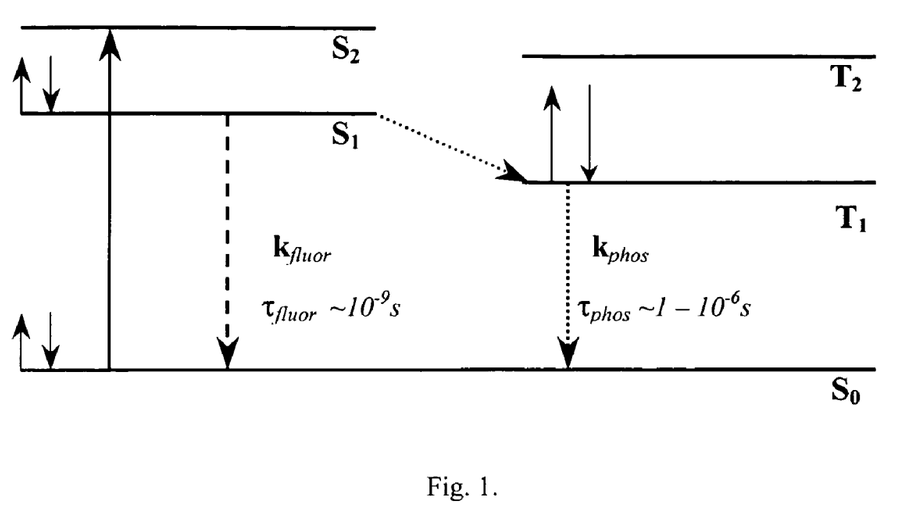
FIG. 1 shows the Jablonski diagram for singlet-singlet and triplet-singlet transitions.

The delayed phosphorescence is explained by non-radiative relaxation from the singlet excited state $S_1$ into the excited triplet state $T_1$ which is followed by a spin-forbidden transition between $T_1$, and the ground state, $S_0$[8]. Phosphorescence is characterized by the lifetime ($\tau$) and quantum yield (Q) of the transition. The lifetime of phosphorescence is strictly dependent on the fluorophore environment, the rigidity of the structure (motility of the fluorophore), type of solvent and pH. A modified Jablonski diagram is shown in FIG. 1 representing the relationships between singlet and triplet states and the transitions responsible for fluorescence and phosphorescence. The phosphorescence spectrum is red shifted relative to fluorescence spectrum.

The phosphorescence data provide important information on dynamical, geometrical and structural changes in protein structure[8,9]. The rigidity of the protein, viscosity of media and low temperatures increase the phosphorescence life-time. The phosphorescence spectra complements the fluorescence data. Using both phosphorescence and fluorescence data of a specimen enhances the detection of changes in biological specimens and/or tissue samples, such as cancerous changes, with a much higher degree of accuracy/sensitivity than fluorescence data alone.

The main components of any biological specimen are proteins. Proteins include the amino-acids bonded together with peptide bonds. The three aromatic amino acids, tryptophan (trp), tyrosine (tyr), and phenylalanine fluoresce in the 300 to 380 nm region, upon excitation in the range from 250 to 300 nm[10]. Trp, due to its stronger absorption and higher quantum efficiency is the predominate fluorophore in this wavelength range. The main emission band of Trp is in the 300 to 400 nm region centered at about 340 nm. Tyr absorption is blue shifted relative to trp absorption; therefore shorter wavelength excitation will enhance tyr emission. Phenylalanine emission is rarely observed in proteins due to very weak absorption in this range[10]. The quantum efficiency and Stokes shift of trp fluorescence is highly depend on protein structure and the local environment[11,12]. The trp absorption spectrum exhibits structure between 250 and 290 nm with principal maxima at 282 and 288 nm, and a shoulder at 265 nm[10]. In water, tyr has absorption maxima at 220 and 275 nm[13]. Tyr fluorescence exhibits a smaller Stokes shift than trp, which is not strongly solvent dependent. The tyr emission maximum is at 305 mm.

Other important natural protein fluorophors in biological tissue are collagen and elastin. The triple helix is a repeating motif in fibril-forming collagens and in range of other extra cellular matrix proteins. This type of structure provided the repeating pattern of $(X-Y-Gly)_n$, where X and Y positions are frequently occupied by Proline (Pro) and Hydroxyproline (Hyp) or Proline (Pro) and Alanine (Ala)[14-16]. The main absorption band of collagen is located at around 340=n and main fluorescence emission band is at around 380 nm. For elastin the main emission fluorescence band is at 410 nm.

Native fluorescence emission of tissue can be from tryptophan (340 nm), collagen (380 nm), elastin (410 nm), NADH (460 nm) and flavins (525 nm).

Human tissue in general has very specific chemical compositions and the fluorescence and phosphorescence spectral signatures of abnormal tissues will be different from normal tissue. Any changes in the normal composition or structure of the human tissue can affect their fluorescence and phosphorescence emission fingerprints. Here we report on phosphorescence of tissues. According to the present invention, selecting key emission wavelengths from the tissue allows one to make a conclusion regarding the normality of the tissue. In other words, if a tissue changes from normal to pre-cancerous or even cancerous, the fluorescence and phosphorescence emission fingerprints detected using the method of the present invention would indicate the change in the tissue that would allow for the classification of the tissue as cancerous or pre-cancerous.

To avoid experimental imperfections related to measurements of absolute intensity values, the ratio of intensities at the emission key wavelengths are calculated. This ratio is a signature of malignancy or normalcy of the tissue. Based on this ratio, a conclusion on whether a tissue is normal/benign, pre-cancerous or cancerous can be determined.

SUMMARY OF THE INVENTION

The present invention is directed to a method for detecting changes in composition and/or structure of a tissue sample comprising of exciting at least a portion of a tissue sample with light from about 280 nm to about 300 nm. Once the tissue is excited by light in the stated range, a fluorescence emission signature of a molecule from at least a portion of the tissue sample is selected. A phosphorescence emission signature of the molecule from the same portion of the tissue sample is also selected. Using the fluorescence and phosphorescence emission signatures obtained, an intensity ratio value can be obtained by dividing the fluorescence emission signature value by the phosphorescence emission signature value. Once the intensity ratio value is calculated it can be compared with predetermined intensity ratio values of normal/benign tissue, pre-cancerous tissue and/or cancerous tissue and used to identify the state of the tissue from which the sample was taken. In other words, if the intensity ratio value obtained is the same as that determined for normal/benign tissue then the tissue can be identified as normal/benign tissue. If the intensity ratio value obtained is the same as that determined for pre-cancerous tissue, the tissue can be identified as being pre-cancerous tissue and finally, if the intensity ratio value obtained is the same as that determined for cancerous tissue then the tissue can be identified as being cancerous.

Another aspect of the invention is directed to a method for detecting cancerous regions within a tissue. Tissue types, which can be interrogated by this invention, include: breast, prostate, gastrointestinal tract, gynecological, renal, lung or brain. This method uses multiple samples taken from a tissue sample located in a dense region of the tissue. One method that can be used to obtain multiple samples from the same tissue uses optical needles capable of taking samples from an area of the tissue that is less than about 0.5 mm.

As a reference point, at least one phosphorescence signal from a predetermined normal/benign area of the tissue to be tested is obtained. A phosphorescence signal from the sample from an area of the tissue to be tested that is different from the area of the tissue used to establish the reference point above is obtained. This phosphorescence signal is compared to the reference phosphorescence signal and determined to be either the same or different. If the sample is the same as the reference point then the sample tissue is identified as being normal/benign.

Yet another aspect of the invention is directed to a method for determining whether a tissue sample is normal/benign, pre-cancerous or cancerous. In this method the tissue sample is excited with light from about 270 nm to about 320 nm to produce an excited tissue. An emission spectrum from the excited sample is detected using different time delays for flourescence emission and for phosphorescence emission. The intensity of the emission spectrum of the excited samples is then compared with predetermined emission spectrums in order to identify whether the tissue sample is normal/benign, pre-cancerous or cancerous tissue.

Still yet another embodiment of the invention is directed to a method for mapping normal/benign, pre-cancerous, and cancerous regions of a tissue comprising exciting a tissue sample with light having a wavelength of from about 270 nm to about 310 nm. A phosphorescence spatial intensity map of the tissue sample at about 500 nm and a fluorescence spatial intensity map of the tissue at about 340 nm are created from the excited tissue. Once the spatial intensities maps are obtained, the maps are compared and the tissue sample is identified as normal/benign, pre-cancerous, or cancerous using the differences between the phosphoresence spatial intensity map of the tissue sample and the fluorescence spatial intensity map of the sample.

Still another aspect of the invention is directed to an optical fiber collection system for collecting emission signals comprising of an optical fiber collection needle configured so as to collect emission signals in an area less than about 0.5 mm and a stage for moving a specimen in at least two directions in order to create a two-dimensional map.

This invention can be implemented using a photo detector sub-system, which disperses light of different wavelengths and then detects the intensity at the wavelengths of interest. The fluorescence and phosphorescence contributions can then be separated by their respective wavelength contributions.

Alternately, this invention can be implemented by using a time gated photo detection system with a adjustable time delay. The fluorescence is detected by setting the time delay between the excitation light pulse and detector gate to zero time. The phosphorescence is detected by setting a delay time between the excitation light pulse and the detector gate. This delay should be longer than the fluorescence lifetime to exclude the collection of fluorescence signal, and the gate width can be set equal to the phosphorescence lifetime to collect all of the phosphorescence signals.

The invention is further described using the figures in the detailed description section below.

DETAILED DESCRIPTION OF THE INVENTION

The emission signatures of certain molecules can be used to determine the state of a tissue and/or organ. In other words, the emission signatures of certain molecules can be used to determine whether the tissue sample (or the tissue itself) is normal/benign, pre-cancerous or cancerous. A representative list of molecules that can be used to determine the state of the tissue includes collagen, elastin, Nicotinamide adenine dinucleotide (NADH), flavins, and tryptophan. Since practically all proteins in human tissue contain tryptophan, the tryptophan emission intensity can be used to characterize most tissues. However, it is understood that the emissions obtained from tryptophan depend on the environment in which the emissions are taken. Any changes in the environment affect the intensity of emission and position of emissions maxima for tryptophan. For example, ultraviolet (UV) excited phosphorescence of tryptophan solution is not easily observed due to quenching by oxygen dissolved in the solvent[17]. Decreasing the temperature of the sample to liquid nitrogen temperatures allowed tryptophan phosphorescence to be observed in many biological samples. Complicated protein structures frequently burry the aromatic amino acids residues within the structure, limiting exposure of amino acids to quenching agents[17, 18]. Tryptophan residues buried within some proteins is the reason why the room temperature phosphorescence from tryptophan can be observed in some specimens. Phosphorescence of tryptophan is very sensitive to any changes in the tryptophan environment, such as oxygenation, pH, etc. Phosphorescence can be used to study the local environmental changes in proteins due to malignancy. Dry tryptophan is not exposed by oxygen dissolved in the solvent and is not usually quenched by other amino acids residues. Therefore, dry tryptophan powder is a good model to study room-temperature phosphorescence of tryptophan in proteins.

Most studies available observed the room temperature phosphorescence of tryptophan and proteins in the 270 to 290 nm excitation range. However, in the present invention tryptophan has been excited at 300 nm, 380 nm and 400 nm using the gating detection described below.

To measure phosphorescence of tryptophan the spectrophotometer, an LS-50B by Perkin-Elmer in delay mode was used. The specimen was excited at 282 nm, 300 nm, 380 nm or 400 nm. The delay time ($T_{del}$) between the light pulse and starting the measurements was changed from 0.5 to 7 ms in 0.5 ms increments. The gate width (time over which data was collected) was kept constant and set to about 1 ms. The phosphorescence emission spectra of tryptophan obtained depends on the excitation wavelength and produces different shapes which reflect different delay times due to different decay time for the transition from triplet to singlet states.

Figure 2:
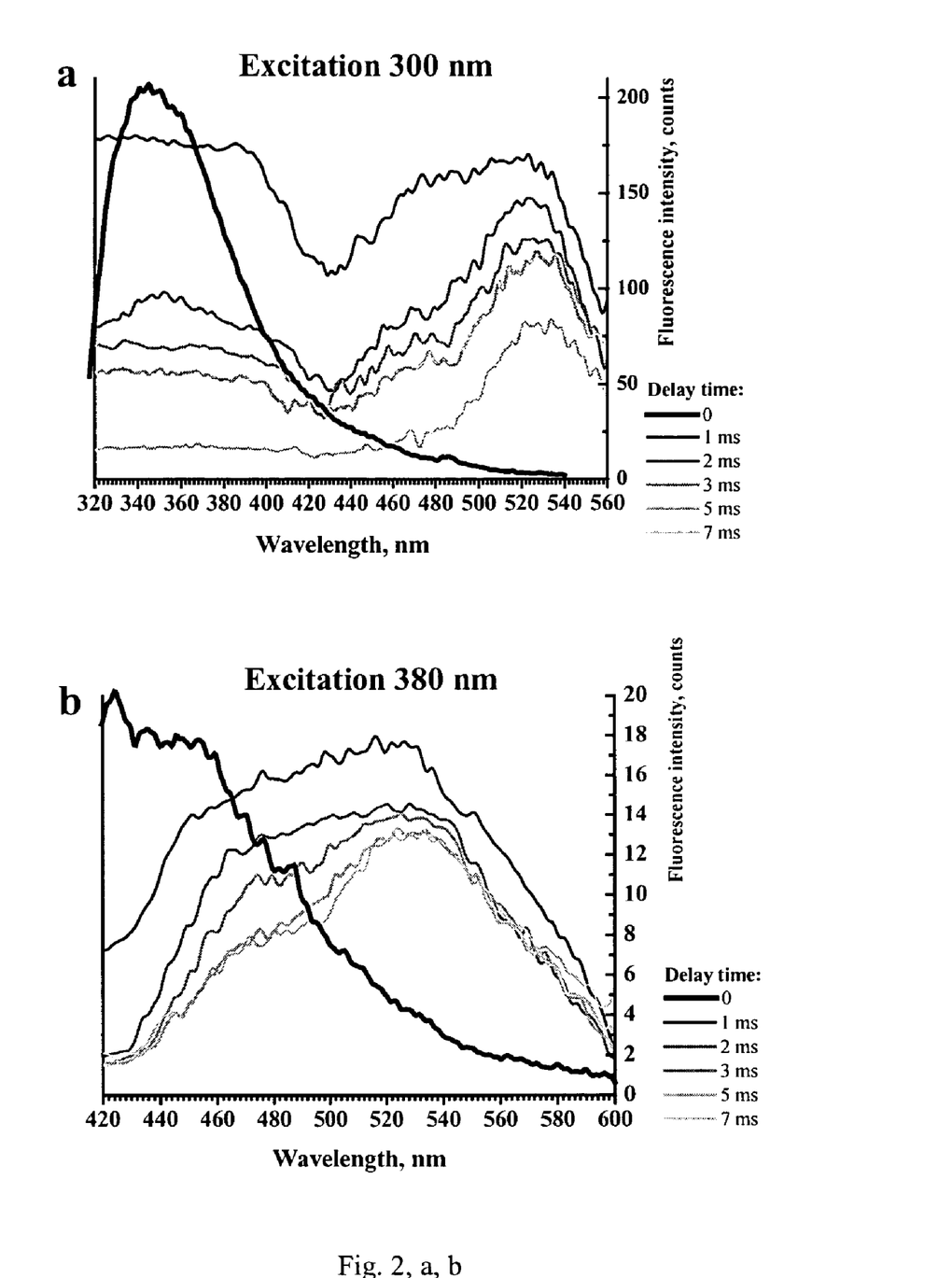
FIG. 2 shows phosphorescence and fluorescence emission of D-L tryptophan powder, measured using time delayed detection collected with 1 ms, 2 ms, 3 ms, 5 ms and 7 ms time delays and a 1 ms gate time. The 0 time delay corresponds to fluorescence emission. The specimen is excited at: a—300 nm; b—380 nm and c—400 nm.

FIG. 2 shows the emission spectra of tryptophan measured with different delayed times $T_{del}$. Excited at 300 nm (FIG. 2 a), tryptophan expresses the fluorescence emission maxima at 340 nm, which can be seen by using a delay time up to 5 ms. At $T_{del}$=0, fluorescence is the main component of the signal. Phosphorescence emission peaks for tryptophan can be seen at 480 nm and 525 nm for longer delay times ($T_{del}$=7 ms) while the fluorescence emission peak at 340 nm can be observed for shorter delay times ($T_{del}$<5 ms) described above. These peaks dominate the emission spectra at long delay times ($T_{del}$) i.e., longer than 2 ms.

Figure 3:
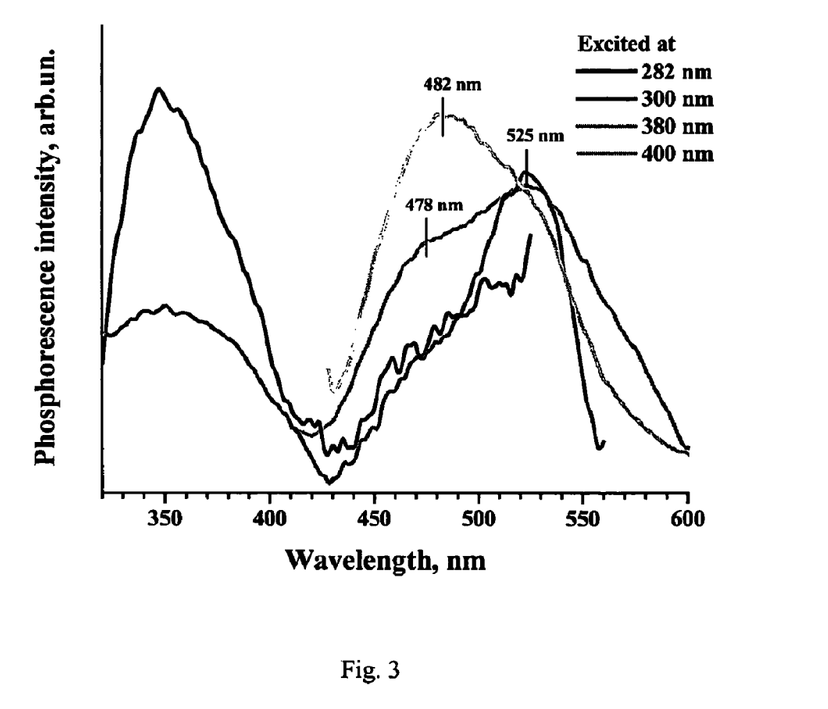
FIG. 3 shows phosphorescence spectra of D-L tryptophan powder acquired with the CD-Scan in phosphorescence mode (delayed detection). Tryptophan was excited at 282 nm, 300 nm, 380 nm and 400 nm. Each spectrum shown represents a time integration from 0.5 ms to 7 ms delay with respect to the excitation light pulse.

Fluorescence emission spectra, measured at $T_{del}$=0, has an emission peak at 340 nm and a weaker, longer wavelength tail in the 400 to 560 nm range. When excited at 380 nm or 400 nm (FIG. 2 b and c), tryptophan provides two phosphorescence emission maxims, one at 480 nm and the other at 525 nm. When the specimen is excited at 380 nm, the 525 nm peak is as the dominant peak in the emission spectra. Excitation at 400 nm provided approximately equal emission intensities for both the 480 and 525 nm peaks for time delay longer than 2 ms. The fluorescence emission spectra ($T_{del}$=0) of a trp powder specimen excited at 380 and 400 nm shows only a background from scattered light. The total (or integrate) phosphorescence spectrum can be obtained by summing the phosphorescence spectra for all gate delay times. The integrated phosphorescence spectra from tryptophan powder are shown in FIG. 3 for excitation at 282, 300, 380 and 400=n, using an integrated detector delay time from 0.5 to 7 ms.

Figure 4:
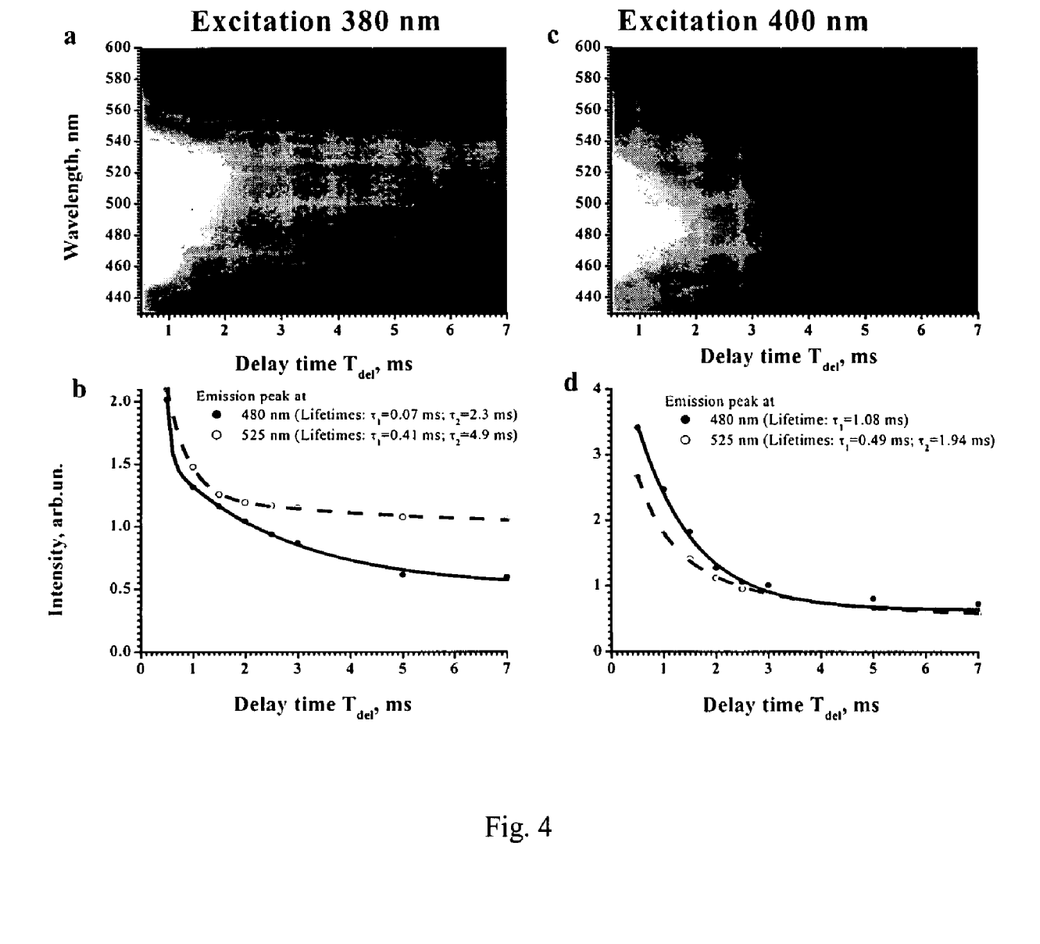
FIGS. 4a and 4c show a 2D map of phosphorescence of D-L tryptophan, excited on 380 nm and 400 nm respectively. The X-axis is delay time, ms; Y-axis is wavelength (in nm)
FIGS. 4b and 4d show a decay curve of phosphorescence emission at the 480 nm and 525 nm wavelengths peaks, wherein the tryptophan powder was excited at 380 nm and 400 nm respectively. The decay curves can be described as double exponential processes. Excited at 380 nm, tryptophan has emission peaks at 480 nm with lifetimes $\tau_1$=70 μsec and $\tau_2$=2.3 ms, and at 525 nm with lifetimes $\tau_1$=0.4 ms. and $\tau_2$=4.9 ms. When excited at 400 nm, the tryptophan has emission peaks at 480 nm with a lifetime $\tau_1$=1.08 ms and at 525 nm with lifetimes $\tau_1$=0.49 ms and $\tau_2$=1.94 ms.

FIG. 4 a, c shows a 3-D map of tryptophan emission wavelength vs. delay time ($T_{del}$) for excitation wavelengths at 380 nm and 400 nm. As can be seen in FIG. 4, tryptophan has strong phosphorescence at 480 nm and 525 nm for excitation longer than 300 nm; for excitation at 282 mm, the phosphorescence emission is much weaker. Two main phosphorescence bands are observed at 480 nm and at 525 mm. For excitation at 300 nm and 380 mm the intensity of 525 nm band is higher than for 480 nm. For excitation at 400 nm the intensity of 480 nm band becomes higher. The phosphorescence decay graph for emission peaks at 525 mm and 480 nm for excitation at 380 nm and at 400 nm are displayed in FIG. 4 b and d. The phosphorescence decay graph can be described as double exponential decay. Excited at 380 nm, tryptophan has emission peaks at 480 nm with lifetimes $\tau_1$=70 μs and Nicotinamide adenine dinucleotide $\tau_2$=2.3 ms and at 525 nm with $\tau_1$=0.4 ms. and $\tau_2$=4.9 ms. Excited at 400 nm, tryptophan has emission peaks at 480 nm with lifetime $\tau_1$=1.08 ms. and at 525 nm with $\tau_1$=0.49 ms. and $\tau_2$=1.94 ms.

Figure 5:
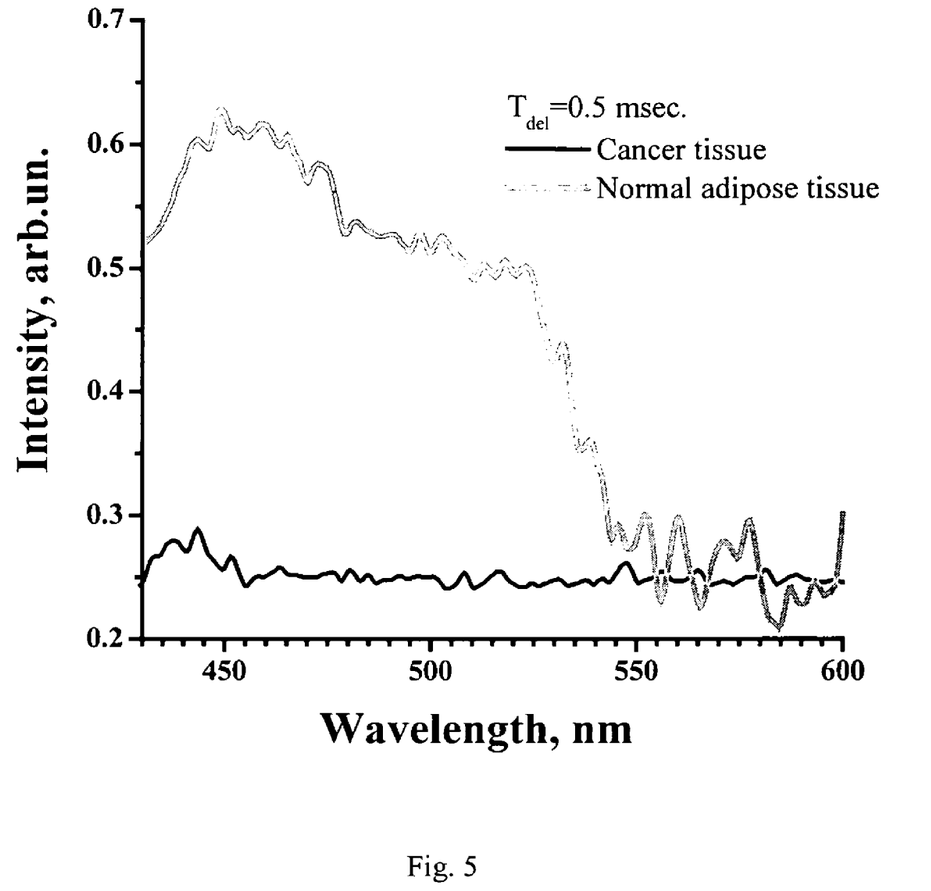
FIG. 5 shows the phosphorescence spectra from normal adipose breast tissue and cancerous breast tissue, excited at 380 nm with a delay time of 1 ms and gate of 5 ms. The measurements were performed using the CD-scan instrument.

FIG. 5 shows the phosphorescence signal from cancer and normal adipose frozen breast tissue excited at 380 nm. Delay time ($T_{del}$) is 0.5 ms; gate ($T_{gate}$) is 5 ms; slit is 14 nm; scanning rate is 60 nm/min. As can be seen from FIG. 5 cancer tissue does not have much of a phosphorescence signature at all, whereas normal tissue has a phosphorescence signature at 450 nm and at 520 nm.

As can be seen from the figures discussed above, the phosphorescence tryptophan spectras are very different for normal and cancer tissues. It is these differences that the present invention uses to distinguish cancerous from normal/benign tissue either in a functioning tissue/organ or to define cancerous areas within the same tissue. Phosphorescence signals can be detected using time delayed emission measurements from excitation flashed light or a time integrated detection where a fluorescence signal will also appear with the phosphorescence signal. The fluorescence signal can be detected using flash excitation and time coincidence (prompt) detection with no delay time.

The present invention is directed to a new method for detecting cancerous and pre-cancerous tissue using the fluorescence and phosphorescence signatures of tryptophan and other molecules (collagen, flavins, NADH, and elastin). Since tryptophan is present in most proteins in human tissue and it is very sensitive to environmental changes, tryptophan can be detected in any human tissue. The fluorescence emission of tryptophan depends greatly on the pH, the environmental conditions, such as temperature, pressure and whether a quencher is present in protein structure. There are many molecules and tissues (such as collagen, NADH flavins and elastin) where phosphorescence can be detected in vivo and in vitro. The phosphorescence depends strongly on the geometrical, structural and dynamic changes in protein molecules, as well as, the changes in the physical environment (temperature, pH, etc.) and the chemical environment (oxygen content). The fluorescence emission signature for tryptophan is around 340 nm, when excited within the 260 to 300 nm range. The phosphorescence signature of tryptophan has a higher quantum yield when excited within the 340 nm to 400 nm range, with a phosphorescence emission maxima at 480 nm and 525 nm. Unfortunately, the excitation of tryptophan at 380 nm or 400 nm does not also provide a fluorescence signature for tryptophan. Therefore, the method of the present invention sacrificed the higher intensity of tryptophan phosphorescence in order to collect both fluorescence and phosphorescence signatures.

The present invention allows one to perform rapid, ex-vivo or in-vivo analysis of biological tissue and distinguish between cancerous and pre-cancerous states of the tissue from a normal/benign state of a tissue using phosphorescence analysis alone or in combination with fluorescence analysis. The present invention can also be used to distinguish cancerous regions from benign/normal regions within the same tissue. The selection of key wavelengths for excitation of the tissue and the use of modern compact high-sensitivity spectrophotometers allows one to receive fluorescence and phosphorescence signatures from the same tissue.

One embodiment of the present invention excites tissue at about 300 nm and both fluorescence and phosphorescence of tryptophan molecules are obtained and analyzed. It is this time delay detection of the phosphorescence emission signal that is used for cancer detection. For example, the ratio of intensities of fluorescence peak at 340 nm and phosphorescence peak at 500 nm from tryptophan provide information about malignancy of the tissue in vitro and can be used in vivo applications. The intensity ratio of a tissue, i.e. higher than 15, corresponds to cancerous tissue in vitro, wherein the intensity ratio in the 5 to 12 range corresponds to normal or benign human adipose breast tissue. An intensity ratio value less than 5, corresponds to normal human glandular breast tissue. These values were measured for in vitro experiments. One can expect that in vivo tissue ratios will follow the same pattern but with potentially different ratio ranges for different tissue status.

The present invention is also directed to the use of video in detecting cancer within a tissue. The use of two-dimensional (2D) translation movements of the specimen or the use of a video detection system in combination with a very precise system of emission collection (optical needle system) allowed one to create 2D intensity ratio maps of the specimen which can be used to precisely locate the malignant area of a tissue, i.e. the highest intensity value indicating a cancerous area, an average intensity value indicating a pre-cancerous area and a low intensity ratio indicating normal or benign tissue.

Figure 6:
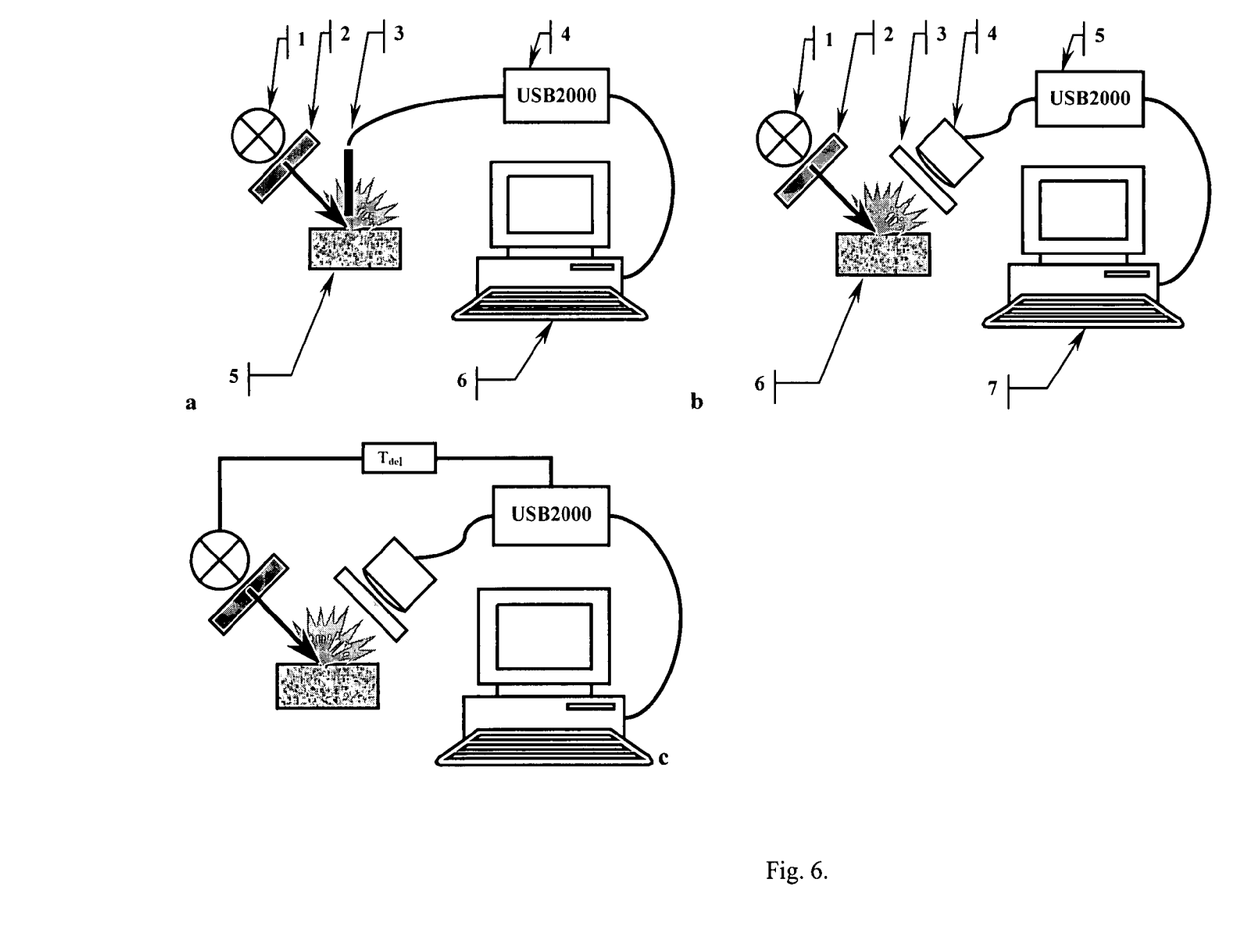
FIG. 6a shows a schematical diagram of the present invention using a precise optical fiber needle collection system.
FIG. 6b shows a schematical diagram of the present invention using a lens collection system.
FIG. 6c shows a time delay ($T_{del}$) system between excitation part and detection system.

Examples of the new, compact optical systems of the present invention that can be used to investigate a malignancy of tissues are shown on FIG. 6. To use these systems, the specimen is excited with ultra violet (UV) to visible light. The source of UV light (1) can be Xe lamp or UV LED. UV LED at 270 to 320 nm range are based on Gain multi-quantum well structures[19, 20]. The excitation source can be pulsed or operated in cw mode. The sample can be excited and the detection system used to detect the signal at prompt ($T_{del}$=0) or time delayed $T_{del}$, ($T_{del}$:0.1 to $10^{-7}$ s). Time gating is used to detect fluorescence and phosphorescence; to detect mainly fluorescence, the $T_{del}<10^{-8}$ sec and to detect mainly phosphorescence a delay time $T_{del}>10^{-6}$ s is used. To select the key excitation wavelengths, the narrow band filters (NBF) (2) are placed in front of a light source. The specimen, excited with UV light, emits the fluorescence and phosphorescence signal. The emission is collected with a collimator coupled with a collecting lens (FIG. 6, b). UV quartz optical fiber connects the collecting system with portable spectrometer (Ocean Optics USB 2000) by SMA connector.

Collected spectra were transferred to a personal computer (PC) through a USB port using OceanOptics software. The Complementary-symmetry/metal-oxide semiconductor (CMOS) linear array can be used to detect both fluorescence and phosphorescence components (FIG. 6, a, b). A time delay system (τ) can be used in connection with pulsed light source (LED or Xe flash lamp) to separately detect the phosphorescence spectra and fluorescence spectra (FIG. 6, c). To separate the emission signatures from the light source signal reflected from the specimen, the razor edge long pass filter (LPF) is placed in front of lens collecting system. To provide high selectivity and increase the accuracy of the measurements, the lens collecting system can be changed to the needle system using quartz optical fiber inside (FIG. 6, a). A fiber optic needle with diameter ~1 mm, is coupled with quartz optical fiber and connected with portable spectrometer. The distance between the specimen and the optical needle is ≦1 mm. A microfilter can be used to solve this difficult problem to put the LPF filter between the needle and the sample. The correct selection of a key wavelength can help to overcome this problem. The excitation source can be Xe flash lamp or pulsed light emitting diode (LED) operated at different wavelength $\lambda_{pump}$, in the 280 to 380 nm range. The fiber optic needle collecting device shown in FIG. 6, a and b uses charge-coupled device (CCD) or CMOS arrays as the detector while, the FIG. 6, c uses time decay $T_{del}$ detection to monitor phosphorescence and fluorescence spectra. Using fiber optics diminishes the size of the area under study and also opens possibility to investigate tissues in-vivo.

The present invention is directed to a new fiber optic collection system for collecting emission signals of a sample comprising an optical fiber collection needle configured so as to collect emission signals in an area less than about 0.5 mm. The device also contains a stage that is capable of moving in at least two directions so as to be able to scan a specimen in at least two directions and create 2D maps. The device can be connected to a computer-processing unit (CPU) so that data can be stored and further processed. The optical fiber collection system may also contain a charge-coupled device (CCD)/Complementary-symmetry/metal-oxide semiconductor (CMOS) llinear array detector for creating phosphorescence spatial intensity maps and fluorescence spatial intensity maps of said specimen.

Figure 7:
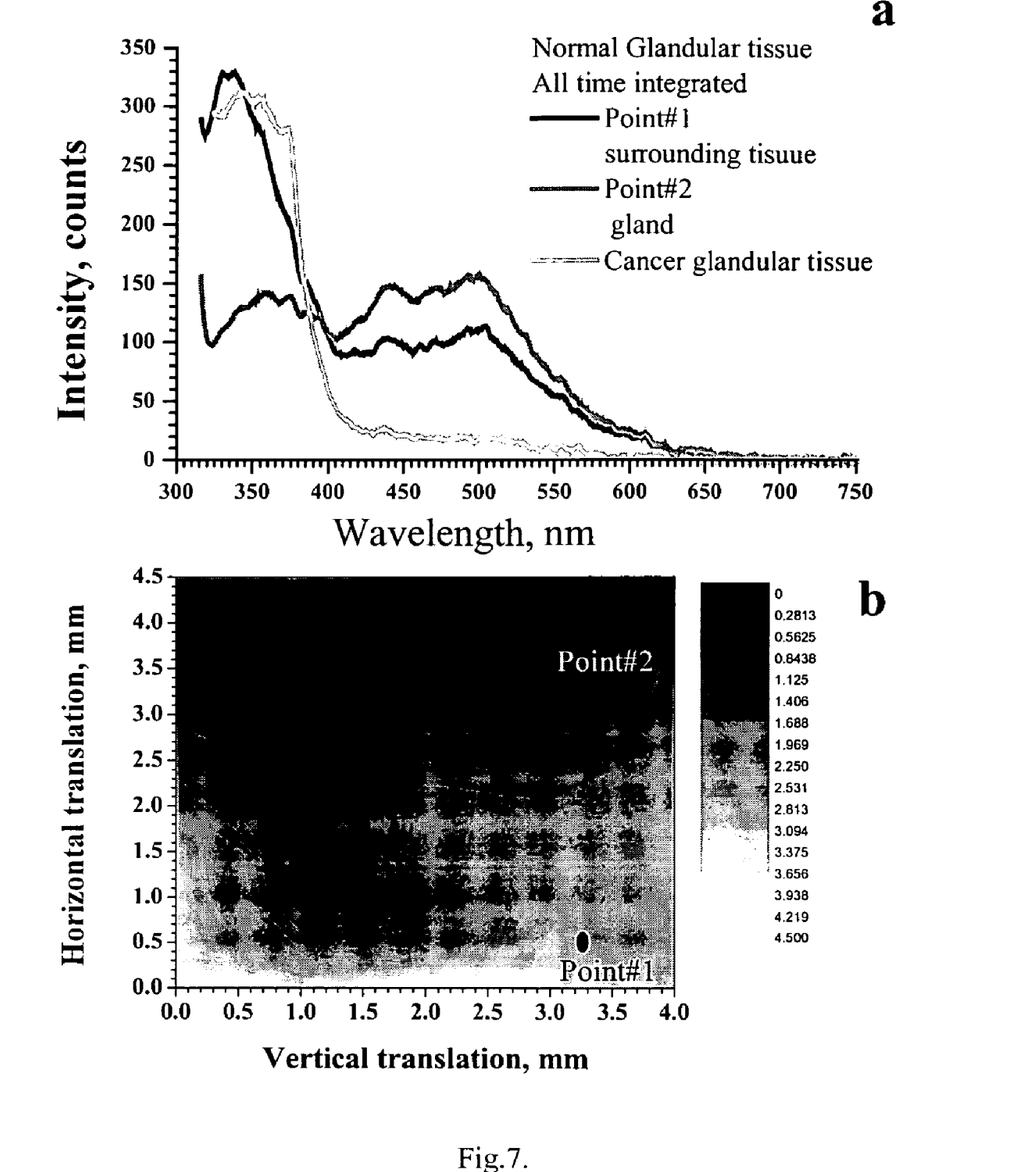
FIG. 7a shows a combined fluorescence and phosphorescence spectra from cancerous and normal glandular tissues received using an optical fiber needle collection system. The spectra of normal tissue were collected from two different points on the specimen.
FIG. 7b shows a 2D intensity ratio spatial map of normal glandular tissue translated with steps of 0.5 mm. The ratio of emission intensity at 340 mm peak to emission intensity of 500 mm peak was calculated for each measurement point.

As stated above, using the 2D translation stage and the optic fiber needle collection system of the present invention, allows for a 2D map of the specimen to be created, using the setup shown in FIG. 6, a. Normal human breast glandular tissue excited at 300 nm was moved along the X-axis and Z-axis of the 2D translational stage in 0.5 mm steps. Three main emission bands were selected from the spectra: the band centered at 340 nm characterizes fluorescence from tryptophan, the band at 440 nm characterizes fluorescence from extra cellular matrix and molecular components and the band at 500 nm is phosphorescence from tryptophan. The ratio of intensities of emission peaks at 340 nm and 500 nm were found for every XZ position in the scanned area of the specimen and a 2D ratio map was created. The ratio obtained varied in the range from 0.2 to 4.5. FIG. 7, a shows the combined phosphorescence and fluorescence emission spectra of normal and malignant (cancer) human breast glandular tissue. As can be seen the emission of normal glandular tissue is very different than the emission from normal/benign human glandular tissue. The quality of the map depends on the precision of measurements.

The normal tissue surrounding the gland shown in FIG. 7 has a higher emission intensity peak centered at 350 nm, than at 450 nm or 500 nm. The gland itself has an equal or lower emission intensity peak centered at 350 nm, than at 450 nm or 500 nm. The cancerous glandular tissue provided strong emission with peak at 350 nm, but emission at 450 nm and 500 nm are close to scattering background. The FIG. 7 b shows the 2D ratio spatial map with highlighted points 1 and 2. The emission spectra of highlighted points 1 and 2 are presented in FIG. 7, a. As can be seen from these 2D spectras, the glands can be easily distinguished from the surrounding glandular tissue. This is because the gland itself has a low intensity ratio value and is depicted on the 2D map as a black area. In contrast, the CD-scan system provided the emission spectra, integrated for large area and could not resolve small features, i.e. gland tissue form surrounding glandular tissue.

Figure 8:
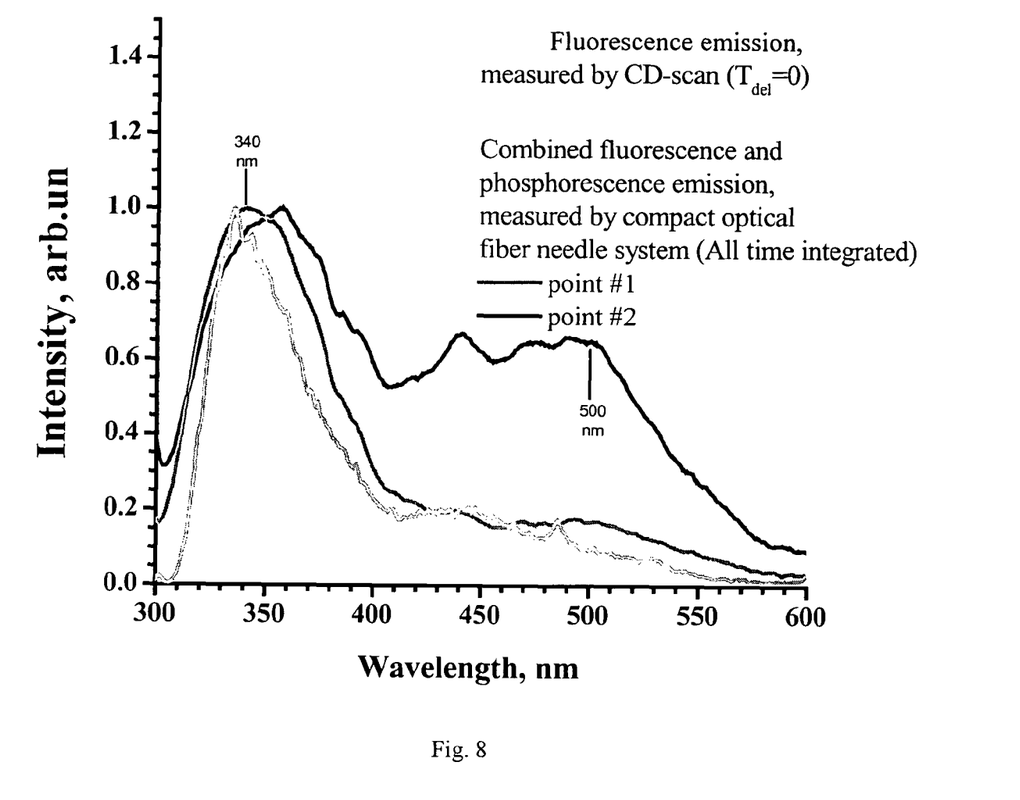
FIG. 8 shows a comparison of the emission spectra of normal glandular breast tissue, measured with the CD-scan ($T_{del}$=0) and with the optical fiber needle system (Ocean Optics spectrometer without time gating). Tissue was excited at 300 mm.

FIG. 8 shows the emission spectra of normal human glandular breast tissue excited at 300 nm, measured using CD-scan system and CFP optical needle system at two points. The spectra were normalized to the emission intensity at 340 nm. Combined fluorescence-phosphorescence spectra (CFP) were found to be very similar to fluorescence the emission spectra obtained using a CD-scan fluorimeter, but the CFP spectra have additional phosphorescence emission peak at 500 nm. Since the gland is very small in size, as compared with the excitation area of the CD-scan instrument, the emission spectra obtained contains information not only from the gland but also from the surrounding tissue. The more precise measurement of the CFP uses the optic fiber needle system of the present invention and provides a better resolution of the area of interest in the biological tissue without including information from much of the surrounding area.

Figure 9:
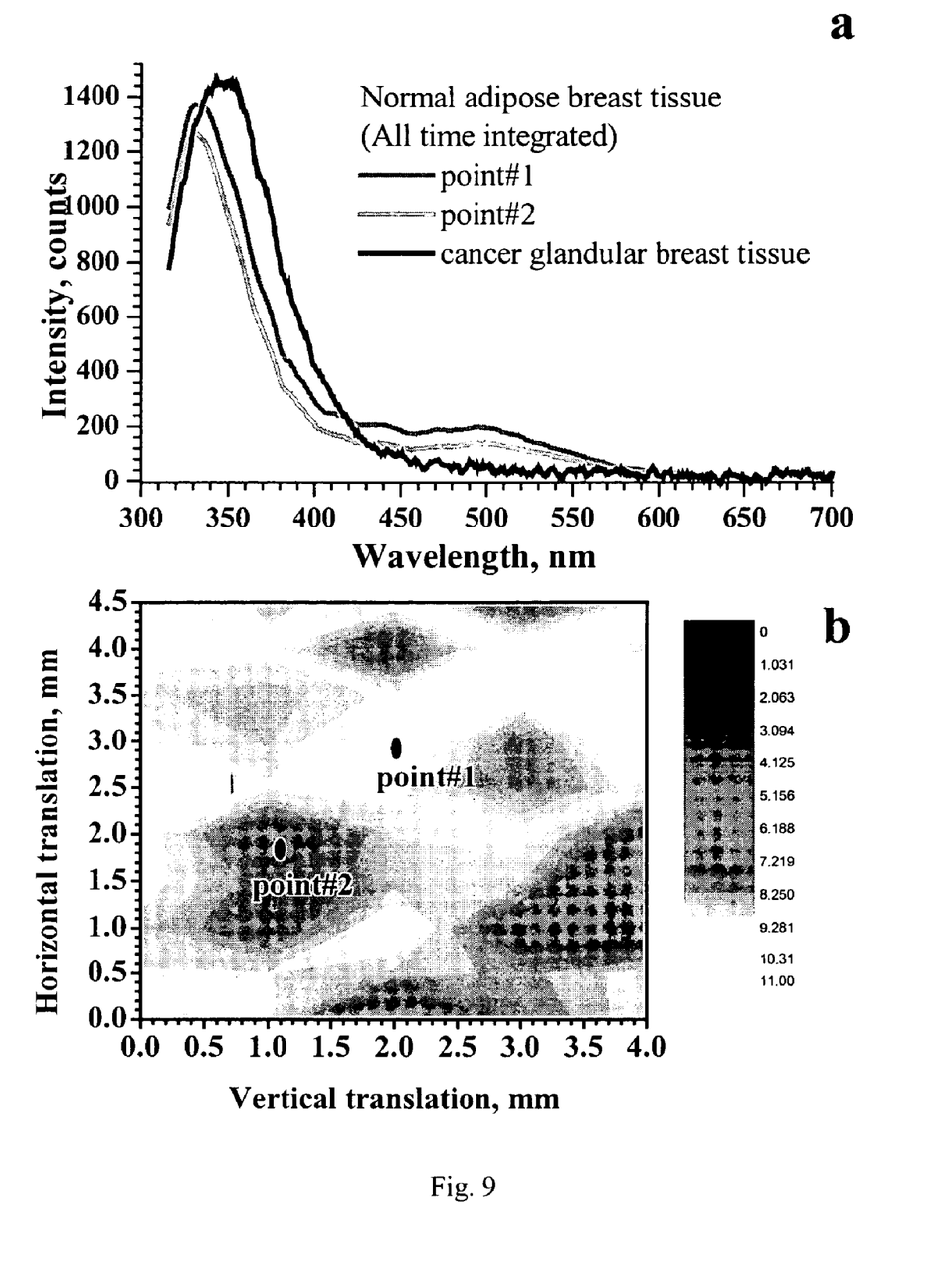
FIG. 9a shows a combined fluorescence and phosphorescence spectra of normal adipose breast tissue and cancerous breast tissue obtained using the optical fiber needle collection system, excited with a 300 mm UV LED and measured with an Ocean Optics spectrometer (with out time gating). The spectra of the normal breast tissue were collected from two different points on the specimen.
FIG. 9b shows a 2D intensities ratio spatial map of normal adipose tissue. The specimen was translated in 0.5 mm steps. The ratio of emission intensity at 340 nm peak to emission intensity of 500 nm peak was calculated for each measurements point.

A 2D intensity ratio map was created for normal human adipose breast tissue and is shown in FIG. 9a. The procedure was the same as for glandular tissue measurements. The normal human adipose tissue shows a very high value of intensity ratios (from 4.5 to 11). FIG. 9, b also shows a 2D map for intensity ratios for normal human adipose breast tissue. Both spectra show the presence of 340 nm fluorescence emission signature and 500 nm phosphorescence emission signature of tryptophan.

Figure 10:
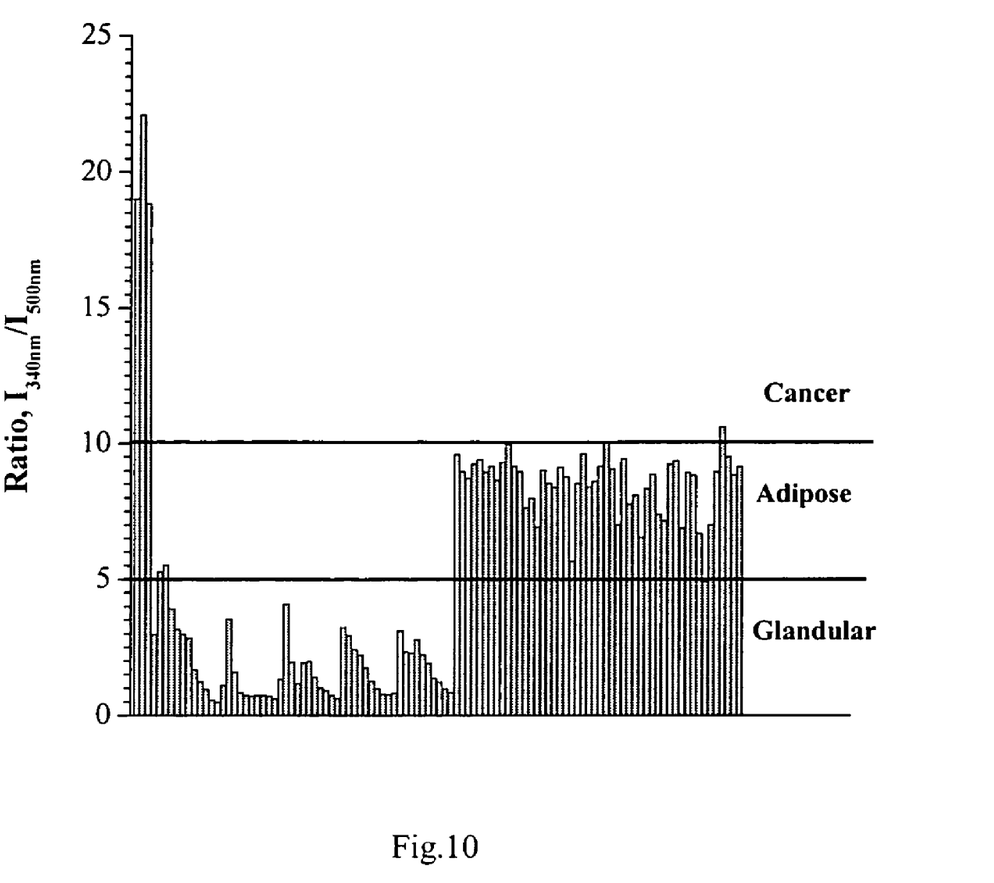
FIG. 10 shows the intensity ratios for normal adipose, normal glandular breast tissues and cancer breast tissues. The ratio of the emission intensity at 340 mm to the emission intensity at 500 mm for each specimen was calculated and is displayed in the Figure. The normal glandular tissue ratio was in the 0.2 to 5.0 range, the ratio for normal adipose tissue was in the range of 5.0 to 10.1, and the range for cancerous tissue was greater than 15, the highest range of the different tissue types.

Cancer breast tissue provides even higher intensities ratio values, than normal adipose and glandular tissues. FIG. 10 shows the value of intensities ratio of $I_{340\ nm}$ to $I_{500\ nm}$ for normal glandular and adipose breast tissue and cancer breast tissues. The glandular tissue ratio varied from 0.2 to 5, the adipose tissue ratio—from 5 to 12 and cancer tissue ratio value is higher, than 19. These results should follow to other tissues: GYN, GI, brain and other in body (prostate, liver, bladder, or kidney, for example).

The selection of key wavelengths for excitation of tissue and use of modern compact high-sensitive spectrophotometer allows one to obtain a precise fluorescence and phosphorescence signature from a tissue. Excitation of a tissue in the range of 280 to 300 nm allows for the detection of cancer in a tissue due to the excitation of fluorescence and phosphorescence from tryptophan and other molecules (collagen, elastin, NADH, flavins) in this range. The use of at least one molecule such as tryptophan makes it possible to detect cancer from the fluorescence and phosphorescence emissions obtained in this range as well as other wavelengths. The ratio of intensities of fluorescence peak at 340 nm and phosphorescence peak at 500 nm from tryptophan provides information about malignancy of the tissue. The ratio, higher than 15, indicates that the tissue is cancer tissue, the ratio in 5 to 12 range corresponds to the normal adipose breast tissue. The ratio, lower than 5, corresponds to the normal glandular breast tissue. Using 2D translation of the specimen with the combination of the very precise system of emission collection (needle system) of the present invention allows the creation of 2D intensities ratio maps of the specimen, which could be used to precisely identify the location of the malignant area of the tissue. This would aid in treating the cancerous area (i.e. with radioactive seeds) while leaving the normal/benign cells of the same tissue alone.

Figure 11:
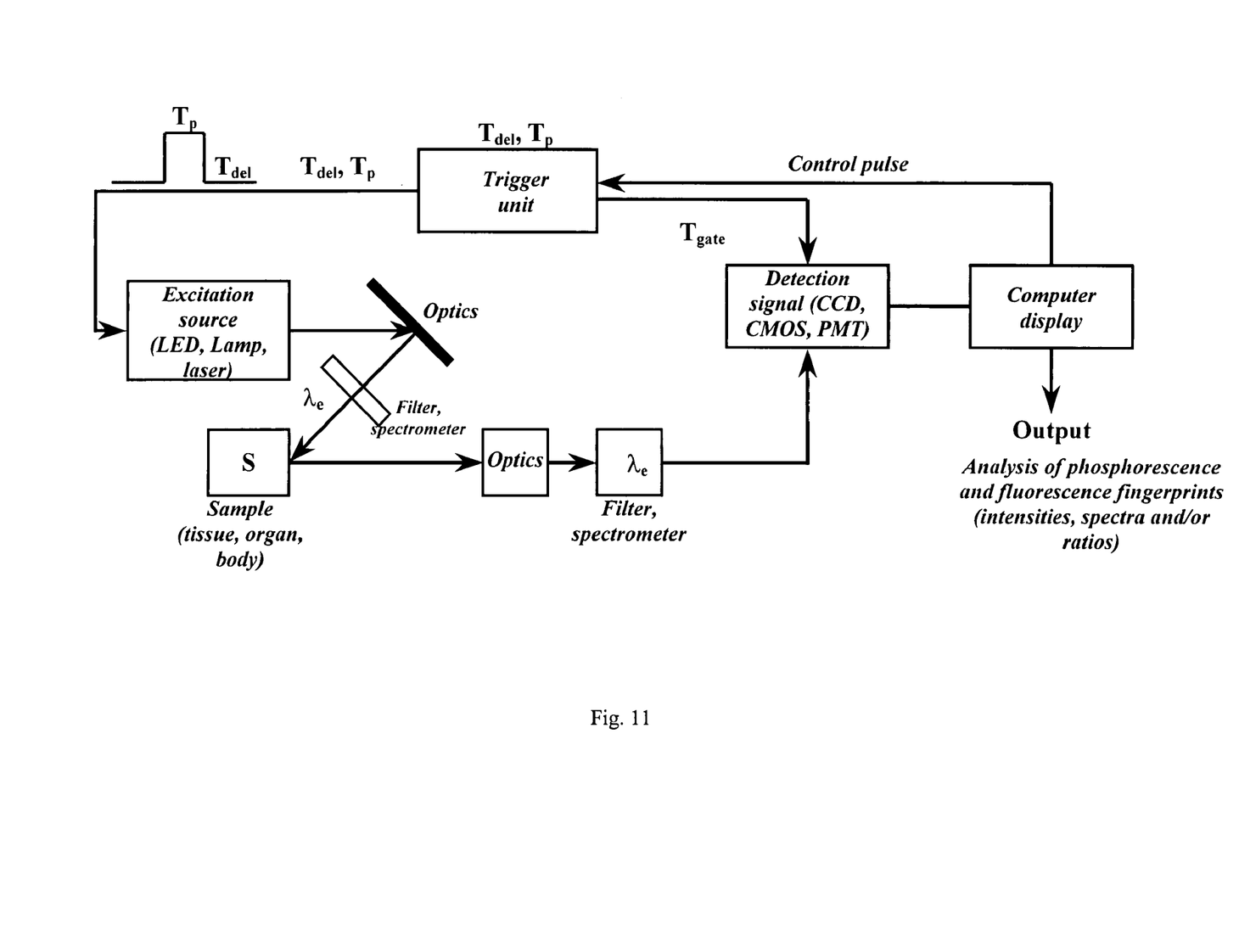
FIG. 11 shows a block diagram of the experimental setup of the present invention.

One principal scheme of the experimental system of present invention is presented in FIG. 11. The pulsed light source used, such as LED, lamp or laser, illuminates the specimen (tissue, organ or body) with UV light having a predetermined pulse length $T_p$. Optics (lens, mirrors) delivering the light to the specimen. The luminescence emission is collected using these optics and delivered to detection unit (CCD, CMOS or PMT). A triggered unit allows the user to separate the phosphorescence emissions (delay time $T_{del}$ is in microsecond, milliseconds or seconds range), and the $T_{del}=0$ (prompt mode) allows the user to operate in prompt mode and collect combined fluorescence and phosphorescence signals. The precise control of these operations and mechanics are conducted using a PC. Output data can be spectra, ratio of emission intensities or emission images at fluorescence and phosphorescence wavelength and can be collected and used to determine the state of the tissue sample as described above.

While the preferred embodiment of the present invention has been illustrated and described in detail, various modifications of, for example, components, materials and parameters, will become apparent to those skilled in the art, and all such modifications and changes are intended to fall within the scope of the claims of the present invention

REFERENCES

1. R. R. Alfano, D. B. Tata, J. Cordero, P. Tomashetsky, F. W. Longo, and M. A. Alfano, "Laser induced fluorescence spectroscopy from native cancerous and normal tissue," IEEE Journal of Quantum Electronics 20, 1507 (1984).

2. R. R. Alfano and M. A. Alfano, "Method for detecting cancerous tissue using visible native luminescence," 4,930,516 (1997).
3. R. R. Alfano and Y. Yang, "Stokes Shift Emission Spectroscopy of Human Tissue and Key Biomolecules," IEEE Journal of Selected Topics in Quantum Electronics 9(2), 148-153 (2003).
4. A. Alimova, A. Katz, R. Podder, G. Minko, H. Wei, R. R. Alfano, and P. Gottlieb, "Virus Particles Monitored by Fluorescence Spectroscopy: A Potential Detection Assay for Macromolecular Assembly," Photochemistry and Photobiology 80(1), 41-46 (2004).
5. A. Alimova, A. Katz, H. E. Savage, M. Shah, G. Minko, D. V. Will, R. B. Rosen, S. A. McCormick, and R. R. Alfano, "Native Fluorescence and Excitation Spectroscopic Changes in Bacillus subtilis and Staphylococcus aureus Bacteria Subjected to Conditions of Starvation," Applied Optics OT 42(19), 4080-4087 (2003).
6. Y. Chen and M. D. Barkley, "Toward understanding tryptophan fluorescence in proteins," Biochemistry 37(28), 9976-9982. (1998).
7. A. Katz, H. E. Savage, S. P. Schantz, S. A. McCormick, and R. R. Alfano, "Noninvasive Native Fluorescence Imaging of Head and Neck Tumors," Technology in Cancer Research and Treatment 1(1), 9-16 (2002).
8. P. Cioni and G. B. Strambini, "Tryptophan phosphorescence and pressure effects on protein structure," Biochimica et Biophysica Acta 1595, 116-130 (2002).
9. D. D. Banks and B. A. Kerwin, "A deoxygenation system for measuring protein phosphorescence," Analytical Biochemistry 324, 106-114 (2004).
10. I. Weinryb and R. F. Steiner, "The Luminescence of the Aromatic Amino Acids," in Excited States of Proteins and Nucleic Acids, R. F. Steiner, ed. (Plenum Press, New York, 1971), pp. 277-319.
11. J. T. Vivian and P. R. Callis, "Mechanisms of tryptophan fluorescence shifts in proteins," Biophys J 80(5), 2093-2109 (2001).
12. D. Creed, "The photophysics and photochemistry of the near-UV absorbing amino acids—I. Tryptophan and its simple derivatives," Photochem Photobiol 39(4), 537-562 (1984).
13. D. Creed, "The photophysics and photochemistry of the near-UV absorbing amino acids—II. Tyrosine and its simple derivatives," Photochem Photobiol 39(4), 563-575 (1984).
14. J. Bella, B. Brodsky, and H. M. Berman, "Hydration structure of a collagen peptide," Nature 3(9), 893-906 (1995).
15. R. Z. Kramer, J. Bella, P. Mayville, B. Brodsky, and H. M. Berman, "Sequence dependent conformational variations of collagen triple-helical structure," Nature, Structural biology 6(5), 454-457 (1999).
16. M. E. Nimni, "Collagen, Structure and function," pp. 877-895.
17. M. L. Saviotti and W. C. Galley, "Room temperature phosphoresence and the dynamic aspects of protein structure," Proc. Nat. Acad. Sci. USA 71(10), 4154-4158 (1974).
18. V. M. Mazhul, E. M. Zaitseva, and D. G. Shcherbin, "Intramolecular dymnamic and functional activity of proteins," Molecular biophysics 45(6), 935-959 (2000).
19. A. A. Allerman, M. H. Crawford, A. J. Fisher, K. H. A. Bogart, S. R. Lee, D. M. Follstaedt, P. P. Provencio, and D. D. Koleske, "growth and desight of deep-UV (240-290 nm) light emitting diodes using AlGaN alloys," Journal of Crystal Growth 272, 227-241 (2004).
20. Q. Li, P. K. Dasgupta, H. Temkin, M. H. Crawford, A. J. Fischer, A. A. Allerman, K. H. Bogart, and S. R. Lee, "Mid-ultraviolet light-emitting diode detects dipicolinic acid," Appl Spectrosc 58(11), 1360-1363 (2004).

What is claimed is:

1. A method for detecting changes in composition and/or structure of a tissue sample comprising:
   (i) exciting at least a portion of the tissue sample with light having a wavelength from about 280 nm to about 300 nm;
   (ii) measuring a native fluorescence emission signature value of a molecule from at least a portion of the tissue sample;
   (iii) measuring a native phosphorescence emission signature value of the molecule from the at least a portion of the tissue sample;
   (iv) determining an intensity ratio value by dividing the native fluorescence emission signature value obtained in step (ii) by the native phosphorescence emission signature value obtained in step (iii);
   (v) determining a difference between the intensity ratio value obtained in step (iv) and one or more predetermined intensity ratio values relating to at least one of a normal/benign tissue, a pre-cancerous tissue and a cancerous tissue;
   (vi) identifying the at least a portion of the tissue as the normal/benign tissue, the pre-cancerous tissue or the cancerous tissue in accordance with the difference between the intensity ratio value and the one or more predetermined intensity ratio values; and
   (vii) generating an intensity ratio map of the tissue sample in accordance with the identification of the at least a portion of the tissue.

2. The method of claim 1 wherein, in the measuring steps, the molecule in which the native fluorescence and the native phosphorescence emission signature values are measured is selected from the group consisting of tryptophan, collagen, flavins, Nicotinamide adenine dinucleotide (NADH) and elastin.

3. The method of claim 1 wherein, in the measuring steps, the molecule for which the native fluorescence and the native phosphorescence emission signatures are measured is tryptophan.

4. The method of claim 1 wherein, in determining the difference between the intensity ratio value and the one or more predetermined intensity ratio values, the one or more predetermined intensity ratio values comprise a first range of values for normal glandular tissue, a second range of values for normal adipose tissue, and a third range of values for pre-cancerous and cancerous tissue, and wherein the first range of values, the second range of values and the third range of values do not overlap.

5. The method of claim 1, wherein, in exciting at least a portion of the tissue sample, the tissue sample is one of human breast tissue, human kidney tissue, human colon tissue, human gastrointestinal tract tissue, human gynecological tract tissue, human cervix tissue, and human oral tissue.

6. The method of claim 1, wherein, in exciting at least a portion of the tissue sample, a light used to excite the tissue sample is generated by a flash lamp, an ultra-violet light device, or Light Emitting Diodes (LED).

7. A method for detecting cancerous regions within a tissue sample comprising:
   (i) exciting at least a portion of the tissue sample to be tested with light from about 280 nm to about 320 nm;

(ii) measuring a native fluorescence emission signature value of a molecule of at least a portion of the tissue sample;
(iii) measuring a native phosphorescence emission signature value of the molecule of the at least a portion of the tissue sample;
(iv) determining an intensity ratio value by dividing the native fluorescence emission signature value obtained in step (ii) by the native phosphorescence emission signature value obtained in step (iii);
(v) determining a difference between the intensity ratio value obtained in step (iv) and at least one predetermined intensity ratio value of a normal/benign tissue area from the same tissue sample;
(vi) identifying the at least a portion of the tissue sample as cancerous or normal/benign in accordance with the difference between the intensity ratio value and the at least one predetermined intensity ratio value; and
(vii) generating an intensity ratio map of the tissue sample in accordance with the identification of the at least a portion of the tissue sample.

8. The method of claim 7 wherein, in determining a difference between the intensity ratio value and at least one predetermined intensity ratio value, the at least one predetermined intensity ratio value of the normal/benign tissue area is a range of about 0.2 to about 5.

9. The method of claim 7 wherein, in identifying the at least a portion of the tissue sample, the at least a portion of the tissue sample is cancerous tissue and the intensity ratio value is between about 5 and about 10.

10. The method of claim 7, wherein, in exciting at least a portion of the tissue sample, a light used to excite the at least a portion of the tissue sample is generated by a flash lamp, an ultraviolet light device, or Light Emitting Diodes (LEDs).

11. The method of claim 7, wherein, in exciting at least a portion of the tissue sample, the tissue sample is one of human breast tissue, human kidney tissue, human colon tissue, human gastrointestinal tract tissue, human gynecological tract tissue, human cervix tissue, and human oral tissue.

12. A method for mapping normal/benign, pre-cancerous, and cancerous regions of a tissue comprising:
(i) exciting the tissue with light having a wavelength at from about 270 nm to about 320 nm;
(ii) creating a native phosphorescence spatial intensity map of the tissue at about 500 nm;
(iii) creating a native fluorescence spatial intensity map of the tissue at about 340 nm;
(iv) identifying one or more of normal/benign, pre-cancerous, and cancerous regions of the tissue by determining intensity ratio values by dividing native fluorescence emission signature values in the native fluorescence spatial intensity map by corresponding native phosphorescence emission signature values in the native phosphorescence spatial intensity map, and determining a difference between the intensity ratio values and one or more predetermined intensity ratio values relating to at least one of a normal/benign tissue, a pre-cancerous tissue and a cancerous tissue.

13. The method for mapping normal/benign, pre-cancerous, and cancerous regions of a tissue of claim 12 wherein at least one optical fiber collection needle that collects samples from the tissue and charge-coupled device (CCD)/Complementary-symmetry/metal-oxide semiconductor (CMOS) linear array detectors that detect native phosphorescence and fluorescence components, in connection with a Computer Processing Unit (CPU), create the native phosphorescence and native fluorescence spatial intensity maps of steps (ii) and (iii) respectively.

14. An optical fiber collection system for collecting native emission signals comprising an optical fiber collection needle adapted so as to collect samples from a tissue and to obtain native emission signals in an area less than about 0.5 mm; a stage for moving a specimen in at least two directions; and a charge-coupled device (CCD)/Complementary-symmetry/metal-oxide semiconductor (CMOS) linear array detector in connection with a Computer Processing Unit (CPU) configured to create native phosphorescence spatial intensity maps and native fluorescence spatial intensity maps of the specimen, and identify one or more of normal/benign, pre-cancerous, and cancerous regions of the tissue in accordance with measured differences in native phosphorescence spatial intensity values in the native phosphorescence spatial intensity map and in accordance with measured differences in native fluorescence spatial intensity values in the native fluorescence spatial intensity map.

15. The optical fiber collection system of claim 14 wherein the CPU controls and records information from the system.

* * * * *